United States Patent
Fischer et al.

(10) Patent No.: US 7,192,276 B2
(45) Date of Patent: Mar. 20, 2007

(54) DENTAL CURING LIGHT ADAPTED TO EMIT LIGHT AT A DESIRED ANGLE

(75) Inventors: Dan E. Fischer, Sandy, UT (US); Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 392 days.

(21) Appl. No.: 10/644,707

(22) Filed: Aug. 20, 2003

(65) Prior Publication Data

US 2005/0042570 A1 Feb. 24, 2005

(51) Int. Cl.
*A61C 3/00* (2006.01)
(52) U.S. Cl. .................................................. 433/29
(58) Field of Classification Search .................. 433/29; 600/245, 249, 199, 200; 362/804
See application file for complete search history.

(56) References Cited

U.S. PATENT DOCUMENTS

| | | |
|---|---|---|
| 3,310,358 A | 3/1967 | Marcatili |
| 3,666,180 A | 5/1972 | Coobs et al. ............ 240/41.15 |
| 3,704,928 A | 12/1972 | Coombs et al. |
| 3,930,149 A | 12/1975 | French |
| 4,184,196 A | 1/1980 | Moret |
| 4,221,994 A | 9/1980 | Friedman et al. |
| 4,229,658 A | 10/1980 | Gonser |
| 4,245,890 A | 1/1981 | Hartman et al. |
| 4,266,535 A | 5/1981 | Moret |
| 4,281,366 A | 7/1981 | Wurster et al. |
| 4,309,617 A | 1/1982 | Long |
| 4,348,180 A | 9/1982 | Schuss |
| 4,385,344 A | 5/1983 | Gonser .................. 362/32 |
| 4,392,827 A | 7/1983 | Martin |
| 4,522,594 A | 6/1985 | Stark et al. |
| 4,611,992 A | 9/1986 | Lokken |
| 4,666,405 A | 5/1987 | Ericson |
| 4,666,406 A | 5/1987 | Kanca, III |
| 4,682,950 A | 7/1987 | Dragan |
| 4,698,730 A | 10/1987 | Sakai et al. |
| 4,733,937 A | 3/1988 | Lia et al. |

(Continued)

FOREIGN PATENT DOCUMENTS

WO    WO 00113608    3/2000

OTHER PUBLICATIONS

U.S. Appl. No. 10/973,537, filed Oct. 26, 2004, Robert R. Scott.

(Continued)

*Primary Examiner*—Cary E. O'Connor
(74) *Attorney, Agent, or Firm*—Workman Nydegger (57) ABSTRACT

A dental device configured for curing light-curable compounds includes an extension portion conforming along a first axis, and a handle portion conforming along an intersecting axis, the axes forming an obtuse angle. An LED light source is disposed on the extension portion, and faces away from the obtuse angle, though rotatable embodiments allow for other configurations. The LED light source may include transilluminating lenses for filtering out undesired radiant energy. The dental device may include finger controls for controlling the emission of light from the LED light source of the dental device. A remote power supply connected with the dental device provides power to the dental device without increasing the size or weight of the dental device.

26 Claims, 7 Drawing Sheets

U.S. PATENT DOCUMENTS

| | | |
|---|---|---|
| 4,836,782 A | 6/1989 | Gonser |
| 4,935,665 A | 6/1990 | Murata |
| 4,948,215 A | 8/1990 | Friedman |
| 4,963,798 A | 10/1990 | McDermott |
| 4,992,045 A | 2/1991 | Beisel |
| 5,013,144 A | 5/1991 | Silverglate et al. |
| 5,013,240 A | 5/1991 | Bailey et al. |
| 5,017,140 A | 5/1991 | Ascher |
| 5,043,634 A | 8/1991 | Rothwell, Jr. et al. |
| 5,046,810 A | 9/1991 | Steiner et al. ............... 385/38 |
| 5,071,222 A | 12/1991 | Laakmann et al. |
| 5,115,761 A | 5/1992 | Hood |
| 5,123,845 A | 6/1992 | Vassiliadis et al. |
| 5,139,495 A | 8/1992 | Daikuzono |
| 5,161,879 A | 11/1992 | McDermott |
| 5,275,564 A | 1/1994 | Vassiliadis et al. |
| 5,285,318 A | 2/1994 | Gleckman |
| 5,288,231 A | 2/1994 | Kuehn et al. |
| 5,290,169 A | 3/1994 | Friedman et al. |
| 5,312,249 A | 5/1994 | Kennedy |
| 5,328,368 A | 7/1994 | Lansing et al. |
| 5,348,552 A | 9/1994 | Nakajima et al. |
| 5,371,826 A | 12/1994 | Friedman |
| 5,382,799 A | 1/1995 | May |
| 5,388,988 A | 2/1995 | Goisser et al. |
| 5,397,892 A | 3/1995 | Abdelqader |
| 5,415,543 A | 5/1995 | Rozmajzl, Jr. |
| 5,420,768 A | 5/1995 | Kennedy |
| D361,382 S | 8/1995 | Brunsell et al. |
| 5,448,323 A | 9/1995 | Clark et al. |
| 5,457,611 A | 10/1995 | Verderber |
| 5,485,317 A | 1/1996 | Perissinotto et al. |
| 5,521,392 A | 5/1996 | Kennedy et al. |
| 5,527,261 A | 6/1996 | Monroe et al. |
| 5,616,141 A | 4/1997 | Cipolla |
| 5,634,711 A | 6/1997 | Kennedy et al. |
| 5,660,461 A | 8/1997 | Ignatius et al. |
| 5,669,769 A | 9/1997 | Disel |
| D385,051 S | 10/1997 | Wu |
| D385,630 S | 10/1997 | Lieb et al. |
| 5,698,866 A | 12/1997 | Doiron et al. |
| 5,711,665 A | 1/1998 | Adam et al. |
| 5,733,029 A | 3/1998 | Monroe |
| 5,749,724 A | 5/1998 | Cheng |
| 5,759,032 A | 6/1998 | Bartel |
| 5,762,605 A | 6/1998 | Cane et al. |
| 5,768,458 A | 6/1998 | Ro et al. |
| 5,772,643 A | 6/1998 | Howell et al. |
| 5,782,553 A | 7/1998 | McDermott |
| 5,791,898 A | 8/1998 | Maissami |
| 5,797,740 A | 8/1998 | Lundvik |
| 5,803,729 A | 9/1998 | Tsimerman |
| 5,880,839 A | 3/1999 | Ishizuka et al. |
| 5,885,082 A | 3/1999 | Levy |
| 5,897,314 A | 4/1999 | Hack et al. ................ 433/29 |
| 5,905,268 A | 5/1999 | Garcia et al. |
| 5,908,294 A | 6/1999 | Schick et al. |
| 5,908,295 A | 6/1999 | Kawata |
| 5,912,470 A | 6/1999 | Eibofner et al. |
| 5,921,777 A | 7/1999 | Dorman |
| 5,971,755 A | 10/1999 | Liebermann et al. |
| 5,975,895 A | 11/1999 | Sullivan |
| 6,001,058 A | 12/1999 | Sano et al. |
| 6,008,264 A | 12/1999 | Ostler et al. |
| 6,019,482 A | 2/2000 | Everett |
| 6,019,599 A | 2/2000 | Völcker et al. |
| 6,028,694 A | 2/2000 | Schmidt |
| 6,033,087 A | 3/2000 | Shozo et al. |
| 6,033,223 A | 3/2000 | Narusawa et al. |
| 6,036,336 A | 3/2000 | Wu |
| 6,059,421 A | 5/2000 | White et al. |
| 6,068,474 A | 5/2000 | Senn et al. |
| 6,077,073 A | 6/2000 | Jacob |
| 6,086,366 A | 7/2000 | Mueller et al. |
| 6,089,740 A | 7/2000 | Forehand et al. |
| 6,095,661 A | 8/2000 | Lebens et al. |
| 6,095,812 A | 8/2000 | Senn et al. |
| 6,099,520 A | 8/2000 | Shimoji |
| 6,102,696 A | 8/2000 | Osterwalder et al. |
| 6,103,203 A | 8/2000 | Fischer |
| 6,123,545 A | 9/2000 | Eggler et al. |
| 6,155,823 A | 12/2000 | Nagel |
| 6,159,005 A | 12/2000 | Herold et al. |
| 6,200,134 B1 | 3/2001 | Kovac et al. |
| 6,208,788 B1 | 3/2001 | Nosov |
| 6,270,343 B1 | 8/2001 | Martin |
| 6,280,187 B1 | 8/2001 | Stone |
| 6,282,013 B1 | 8/2001 | Ostler et al. |
| 6,318,996 B1 | 11/2001 | Melikechi et al. |
| 6,322,358 B1 | 11/2001 | Senn et al. |
| 6,325,623 B1 | 12/2001 | Melnyk et al. |
| 6,328,456 B1 | 12/2001 | Mize |
| 6,331,111 B1 | 12/2001 | Cao |
| 6,361,192 B1 | 3/2002 | Fussell et al. |
| 6,361,489 B1 | 3/2002 | Tsai |
| 6,398,398 B1 | 6/2002 | Moschkowitz |
| 6,402,511 B1 | 6/2002 | Calderwood |
| 6,417,917 B1 | 7/2002 | Jung et al. |
| 6,419,483 B1 | 7/2002 | Adam et al. |
| 6,439,888 B1 | 8/2002 | Boutoussov et al. |
| 6,465,961 B1 | 10/2002 | Cao |
| 6,468,077 B1 | 10/2002 | Melikechi et al. |
| 6,478,447 B2 | 11/2002 | Yen |
| 6,482,004 B1 | 11/2002 | Senn et al. |
| 6,485,301 B1 | 11/2002 | Gemunder et al. |
| 6,511,317 B2 | 1/2003 | Melikechi et al. |
| 6,511,321 B1 | 1/2003 | Trushkowsky et al. |
| 6,514,075 B1 | 2/2003 | Jacob |
| 6,522,086 B2 | 2/2003 | Gemunder et al. ......... 315/291 |
| 6,611,110 B1 | 8/2003 | Fregoso |
| 6,635,363 B1 | 10/2003 | Duclos et al. ............ 428/690 |
| 6,666,875 B1 | 12/2003 | Sakurai et al. ............ 606/169 |
| 6,692,251 B1 | 2/2004 | Logan et al. |
| 6,692,252 B2 | 2/2004 | Scott |
| 6,702,576 B2 | 3/2004 | Fischer et al. ............... 433/29 |
| 6,709,128 B2 | 3/2004 | Gordon et al. |
| 6,719,558 B2 | 4/2004 | Cao |
| 6,719,559 B2 | 4/2004 | Cao |
| 6,755,647 B2 | 6/2004 | Melikechi et al. ........... 433/29 |
| 6,755,648 B2 | 6/2004 | Cao |
| 6,755,649 B2 | 6/2004 | Cao |
| 6,783,362 B2 | 8/2004 | Cao ........................... 433/29 |
| 6,890,175 B2 | 5/2005 | Fischer et al. ............... 433/29 |
| 6,940,659 B2 | 9/2005 | McLean et al. ............ 359/709 |
| 2001/0038992 A1 | 11/2001 | Otsuka |
| 2001/0046652 A1 | 11/2001 | Ostler et al. |
| 2001/0055451 A1 | 12/2001 | Kubara et al. |
| 2002/0073921 A1 | 6/2002 | Russell et al. |
| 2002/0085372 A1 | 7/2002 | Lehrer |
| 2002/0093833 A1 | 7/2002 | West |
| 2002/0102513 A1 | 8/2002 | Plank |
| 2002/0115037 A1 | 8/2002 | Cao |
| 2002/0133970 A1 | 9/2002 | Gordon et al. |
| 2002/0147383 A1 | 10/2002 | Weber et al. |
| 2002/0163317 A1 | 11/2002 | Cao |
| 2002/0167283 A1 | 11/2002 | Cao |
| 2002/0168306 A1 | 11/2002 | Cao |
| 2002/0168604 A1 | 11/2002 | Cao |
| 2002/0168605 A1 | 11/2002 | Cao |
| 2002/0168606 A1 | 11/2002 | Cao |
| 2002/0168607 A1 | 11/2002 | Cao |
| 2002/0168608 A1 | 11/2002 | Cao |
| 2002/0172912 A1 | 11/2002 | Cao |
| 2002/0172913 A1 | 11/2002 | Cao |

| | | |
|---|---|---|
| 2002/0172914 A1 | 11/2002 | Cao |
| 2002/0172915 A1 | 11/2002 | Cao |
| 2002/0172916 A1 | 11/2002 | Cao |
| 2002/0172917 A1 | 11/2002 | Cao |
| 2002/0175352 A1 | 11/2002 | Cao |
| 2002/0175628 A1 | 11/2002 | Cao |
| 2002/0177095 A1 | 11/2002 | Cao |
| 2002/0177096 A1 | 11/2002 | Cao |
| 2002/0177099 A1 | 11/2002 | Cao |
| 2002/0180368 A1 | 12/2002 | Cao |
| 2002/0181947 A1 | 12/2002 | Cao |
| 2002/0182561 A1 | 12/2002 | Cao |
| 2002/0182562 A1 | 12/2002 | Cao |
| 2002/0187454 A1 | 12/2002 | Melikechi et al. |
| 2002/0187455 A1 | 12/2002 | Melikechi et al. |
| 2002/0190659 A1 | 12/2002 | Cao |
| 2002/0190660 A1 | 12/2002 | Cao |
| 2002/0197582 A1 | 12/2002 | Cao |
| 2003/0001507 A1 | 1/2003 | Cao |
| 2003/0036031 A1 | 2/2003 | Lieb et al. |
| 2003/0038291 A1 | 2/2003 | Cao |
| 2003/0039119 A1 | 2/2003 | Cao |
| 2003/0039120 A1 | 2/2003 | Cao |
| 2003/0039122 A1 | 2/2003 | Cao |
| 2003/0040200 A1 | 2/2003 | Cao |
| 2003/0081430 A1 | 5/2003 | Bocker |
| 2003/0133203 A1 | 7/2003 | McLean et al. |
| 2003/0133298 A1 | 7/2003 | Cao |
| 2003/0142413 A1 | 7/2003 | McLean et al. |
| 2003/0147254 A1 | 8/2003 | Yoneda et al. |
| 2003/0147258 A1 | 8/2003 | Fischer et al. |
| 2003/0148242 A1 | 8/2003 | Fischer et al. |
| 2003/0152885 A1 | 8/2003 | Dinh |
| 2003/0186195 A1 | 10/2003 | Comfort et al. |
| 2003/0215766 A1 | 11/2003 | Fischer et al. |
| 2003/0218880 A1 | 11/2003 | Brukilacchio |
| 2003/0219693 A1 | 11/2003 | Cao |
| 2003/0219694 A1 | 11/2003 | Bianchetti et al. |
| 2003/0235800 A1 | 12/2003 | Qadar |
| 2004/0033033 A1 | 2/2004 | Hoshino et al. |
| 2004/0076921 A1 | 4/2004 | Gofman et al. ............... 433/29 |
| 2004/0101802 A1 | 5/2004 | Scott .......................... 433/29 |
| 2004/0121280 A1 | 6/2004 | Fischer et al. ................. 433/29 |
| 2004/0152038 A1 | 8/2004 | Kumagai et al. ............. 433/29 |
| 2004/0201980 A1 | 10/2004 | Fischer et al. ................. 362/84 |
| 2004/0203312 A1 | 10/2004 | Bortscheller et al. ......... 445/24 |
| 2004/0214131 A1 | 10/2004 | Fischer et al. ................. 433/29 |
| 2005/0136372 A1 | 6/2005 | Fischer et al. ................. 433/29 |
| 2005/0142514 A1 | 6/2005 | Scott .......................... 433/29 |
| 2006/0084028 A1* | 4/2006 | Cheetham et al. ............ 433/29 |

OTHER PUBLICATIONS

U.S. Appl. No. 11/184,433, filed Jul. 19, 2005, Robert R. Scott
U.S. Appl. No. 11/200,988, filed Aug. 10, 2005, Robert R. Scott.
U.S. Appl. No. 11/294,159, filed Dec. 5, 2005, Robert R. Scott.
U.S. Appl. No. 60/304,324, filed Jul. 10, 2001, Densen Cao.
"LUXoMAX the Latest News from Akeda Dental," Akeda Dental A/S, www.akeda.dk (Oct. 1, 2001).
"New Sandia UV LEDs emit short-wavelength, high power output," Sandia Laboratories, http://www.eurekalert.org/pub_releases2003-11/dnl-nsu111803.php (Nov. 18, 2003).

* cited by examiner

DENTAL CURING LIGHT ADAPTED TO EMIT LIGHT AT A DESIRED ANGLE

BACKGROUND OF THE INVENTION

1. The Field of the Invention

The present invention relates generally to the field of light-curing devices and, more specifically, to handheld dental light-curing devices incorporating one or more light sources.

2. The Relevant Technology

In the field of dentistry, dental cavities are often filled and/or sealed with photosensitive compounds that are cured when they are exposed to radiant energy, such as visible light. These compounds, commonly referred to as light curable compounds, are placed within dental preparations or onto dental surfaces where they are subsequently irradiated by a light curing dental device. Many light-curing devices are configured with a fiber optic light guide for directing light from a light source into a patient's mouth. The light source may comprise, for example, a lamp, a halogen bulb or a light-emitting diode (LED). One end of the light guide is placed close to the light source so that the light emitted from the light source will be directed into the light guide.

Existing light curing devices are configured to emit adequate light from one or more light sources into a patient's mouth and in a manner that is suitable to cure the light curable compounds. Typically, at least a portion of the light curing device is inserted within the patient's mouth proximate to a dental preparation to help ensure the light is dispersed at the desired location.

Existing light-curing devices, however, provide the operator a somewhat limited range of access to dental preparations within the patient's mouth. Some dental curing lights are rather bulky in size, which makes such devices difficult to insert into hard-to-reach places within a patient's mouth. Others are shaped to facilitate access to some of a patient's teeth but, due to the multiplicity of tooth surfaces and sides that may need to be illuminated, there is currently no design that can facilitate easy access to all or a substantial number of such surfaces and sides. Failure to adequately or evenly illuminate a composite resin filling material can result in improper curing and, possibly, complete or partial failure of the composite filling.

Accordingly, there is an ongoing need in the art for improved dental curing lights that are configured so as to facilitate access to a greater number of surfaces or sides of a patient's teeth.

SUMMARY OF PRESENTLY PREFERRED EMBODIMENTS

Briefly summarized, preferred embodiments of the present invention describe improved dental curing lights that are designed to facilitate access to the sides and surfaces of a patient's teeth during a dental procedure. The invention provides ergonomic design and/or adjustability to accomplish this benefit.

In one aspect of the invention, a dental curing light is provided that is ergonomically designed so that a dental practitioner can hold the curing light in a comfortable fashion while accessing a desired tooth surface or side during a dental procedure. According to one embodiment, a dental curing light is provided that comprises a body having a handle portion that can be gripped or held by the dental practitioner and an extension portion that includes a light source and that is offset at a predetermined angle relative to the handle portion so as to facilitate placement of the light source near a tooth surface or side being illuminated.

In a preferred embodiment, the dental curing light is sized and configured so as to approximate a standard dental hand piece. In this embodiment, the extension portion is offset from the handle portion by a standard contra angle and the light source emits light from a side of the extension portion (e.g., the light source emits light approximately perpendicular to the extension portion). In an alternative embodiment, the angle at which the extension portion is offset from the handle portion may be adjustable.

In another aspect of the invention, which may be in addition to or instead of the aforementioned ergonomic design, a dental curing light is provided that has a light emitting portion that is rotatable relative to a handle portion in order to emit light at different rotational angles relative to the handle portion. In a preferred embodiment, the light emitting portion (e.g., the extension portion) will be locked or restrained from rotating relative to the handle portion during a dental procedure by rotation restraint means (e.g., a mechanical locking device or friction fit). In this way, the light emitting portion is restrained from undesirably rotating out of the desired rotational angle when in use.

The dental curing light may comprise any known light source, or any light source that may be developed in the future, that is suitable for emitting a desired quantity and quality of light. According to one embodiment, the light source comprises at least one LED or LED array. LEDs have the advantage of emitting intense light while using less power compared to other light sources currently available in the art. Not only are LEDs more efficient from the standpoint of power consumption but they generate less heat, thereby increasing comfort for both the patient and dental practitioner.

The dental curing light may further comprise control means that provide desired functionality, such as the duration and intensity of the light emitted by the curing light. The control on the dental device. The control means may include, for example, one or more buttons within the handle portion.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

A detailed description of the inventive dental device will now be provided with specific reference to figures illustrating preferred embodiments. It will be appreciated that like structures will be provided with like reference designations.

Figure 1A:
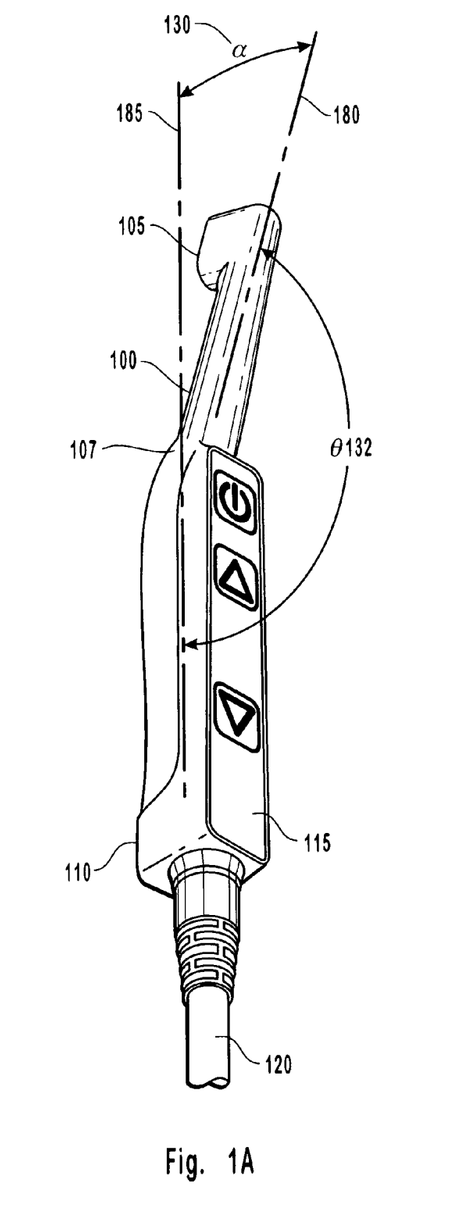
FIGS. 1A–1B illustrate side perspective views of one embodiment of the dental device of the invention that includes a slender body configured in the general shape and size of a dental hand piece, extending from a handle portion through an extension portion, with an LED light source disposed on the extension portion, and a power cord connected at the handle portion.
Figure 1B:
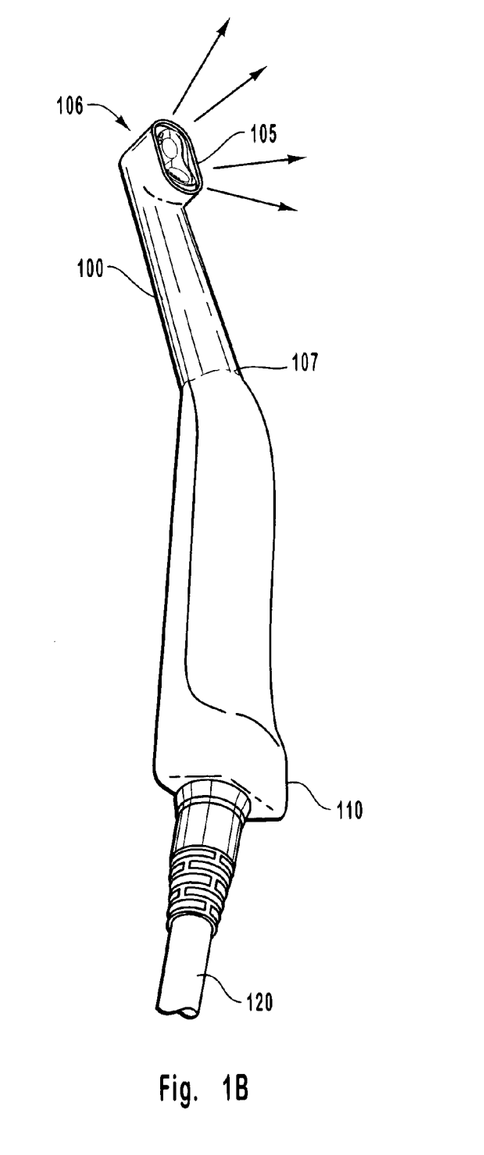

FIGS. 1A and 1B show an embodiment of the present invention having extension portion 100 conforming substantially along a first longitudinal axis or plane 180, and a handle portion 110 conforming substantially along a second longitudinal axis or plane 185. A bend (or joint) portion 107 between the handle portion 110 and extension portion 100 eventuates along longitudinal axis 180. Extension portion 100 comprises light source 105 and extends essentially into joint portion 107. The extension portion 100 and handle portion 110 may be of a continuous form, or separable at joint portion 107, as will be detailed hereinafter. The device may further comprise light controls 115, shown optionally disposed on handle portion 110, and may also comprise a power source, such as cord 120.

As shown in FIG. 1A, the intersection of the longitudinal axes (or planes) 180 and 185 forms an acute angle α 130, and a corresponding obtuse angle θ 132. Stated alternatively, the handle longitudinal axis 185 is laterally offset by the extension longitudinal axis 180, forming the acute angle α 130 (e.g., the standard contra angle of a dental hand piece, which is 17.5°), and the corresponding obtuse angle θ 132. In FIG. 1, light source 105 faces essentially laterally toward handle axis 185, or into the plane formed by the acute angle α 130. The degree of the acute angle α 130 may be predetermined, or adjustable in a variety of conformations, as will be illustrated in one or more of the following figures. Regardless, the light source 105 directs light in a contra angle formation with respect to the overall device. The contra position may be beneficial in at least one respect because it may provide a more natural reach to certain curved portions of the patient's mouth. FIG. 1B shows simply an opposite side perspective view of the FIG. 1A.

As shown in FIG. 1B, the light exiting the light source 105 may exit at a variety of essentially lateral directions, though in some embodiments the exit angle(s) of the light will be focused to a minimal number of exiting directions, such as essentially perpendicular to the handle axis 180. Or as detailed more fully in FIG. 9B, the light source 105 may pivot such that, although the light source 105 is focused, the light source may be directed to a variety of lateral directions with respect to the extension portion longitudinal axis 185. Thus, while the light exiting the light source 105 may be said in this specification and following claims to be perpendicular (or focused, or directed) to either the handle 110 longitudinal axis 185 or the extension 100 longitudinal axis 180, one will appreciate that the light may be directed to or from either axis at a less than perpendicular angle.

Figure 2A:
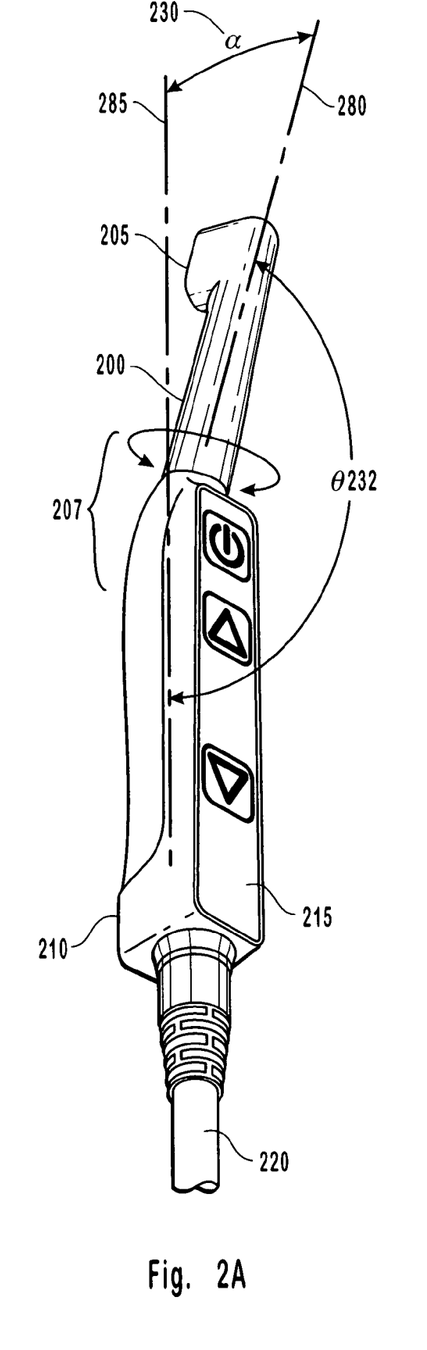
FIGS. 2A–2C illustrate different perspective views of one embodiment of the inventive dental device showing rotation capability.
Figure 2B:
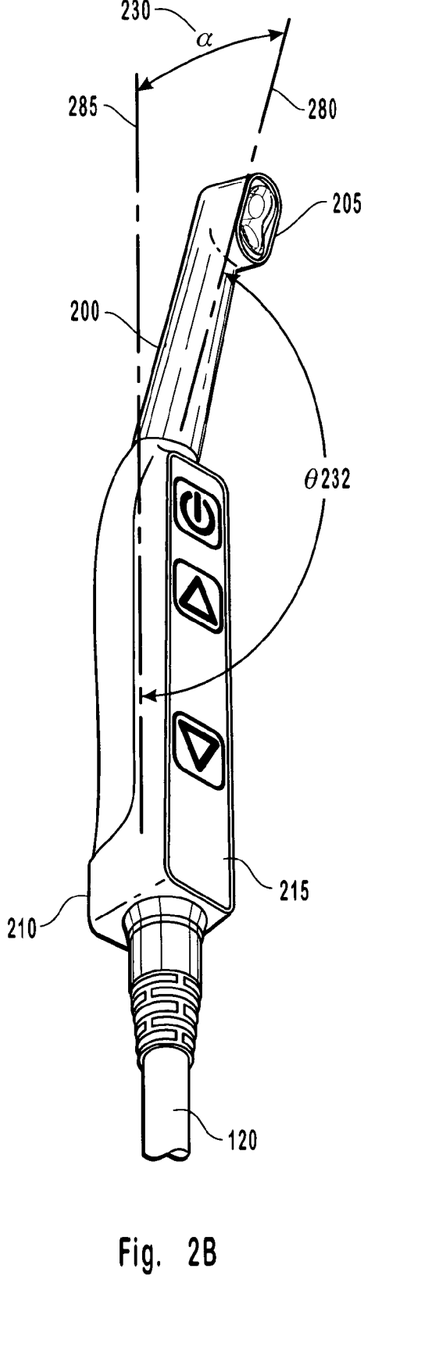
Figure 2C:
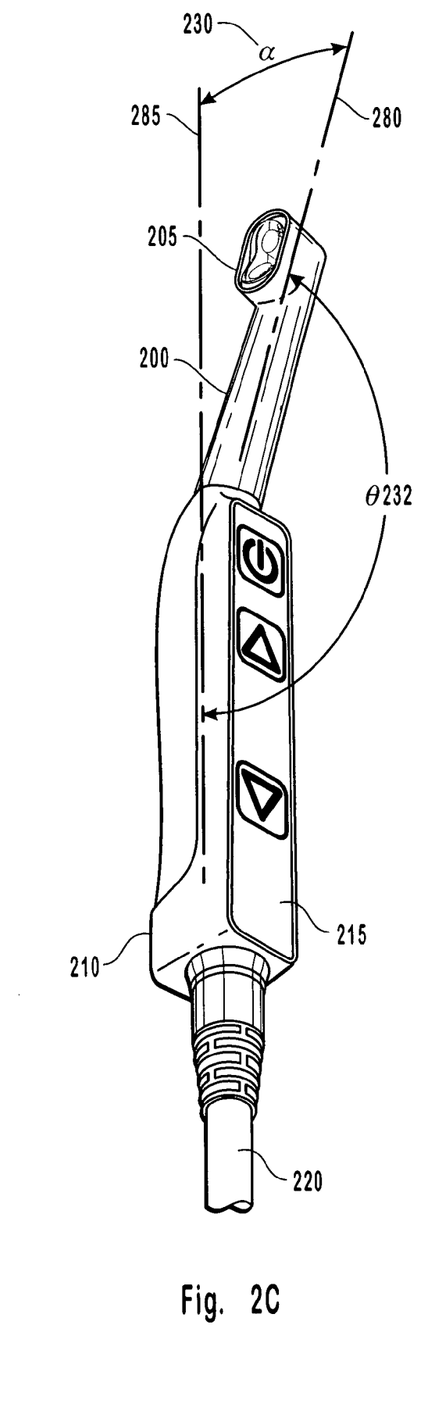

FIG. 2A shows a rotatable version of FIGS. 1A–B, and a variety of rotation conformations of extension portion 200 relative to handle portion 210. For example, FIGS. 2A–2C show extension portion 200 with light source 205 disposed thereon, conforming substantially along longitudinal axis or plane 280, and extension portion 200 further connected with handle portion 210 via joint portion 207. Handle portion 210 conforms substantially along longitudinal axis 285, and is shown with optional light controls 215, as well as shown connected to power source (or cord) 220. In contrast to FIG. 1A however, extension portion 200 is independently rotatable (at joint portion 207) from gripping portion or handle portion 210. FIG. 2A shows also shows the intersection of longitudinal axis 285 and longitudinal axis 280 forming an acute angle α 230, and an obtuse angle θ 232. Light source 205 is shown in the contra angle position, meaning, in this case, that it is positioned bending away from the handle longitudinal axis 285, and at the same time directing light in the direction of longitudinal, handle axis 285, or away from the plane formed by the obtuse angle θ 232.

In addition, because a user can rotate extension portion 200 with respect to handle portion 210, a user can rotate the light source in or out of the contra angle position. For example, FIG. 2B shows the device rotated to 180 degrees with respect to FIG. 2A. In FIG. 2B, light source 205 would be considered facing away from handle axis 285, or away from the plane formed by the acute angle α 230, and facing into the plane formed by the obtuse angle θ 232, and hence not in the contra angle position. FIG. 2C shows the light source rotated 90 degrees such that the light faces in a direction essentially perpendicular to the hypothetical planes formed by the intersection of the longitudinal axes 285 and 280, and hence perpendicular to both of the planes formed by the acute angle 230 and the obtuse angle 232. Of course, the device may be configured to rotate extension portion 200 in 360 individual degree increments, or several degree sets such as 45 degrees, 90 degrees, 180 degrees etc. The invention is not so limited.

Figure 3:
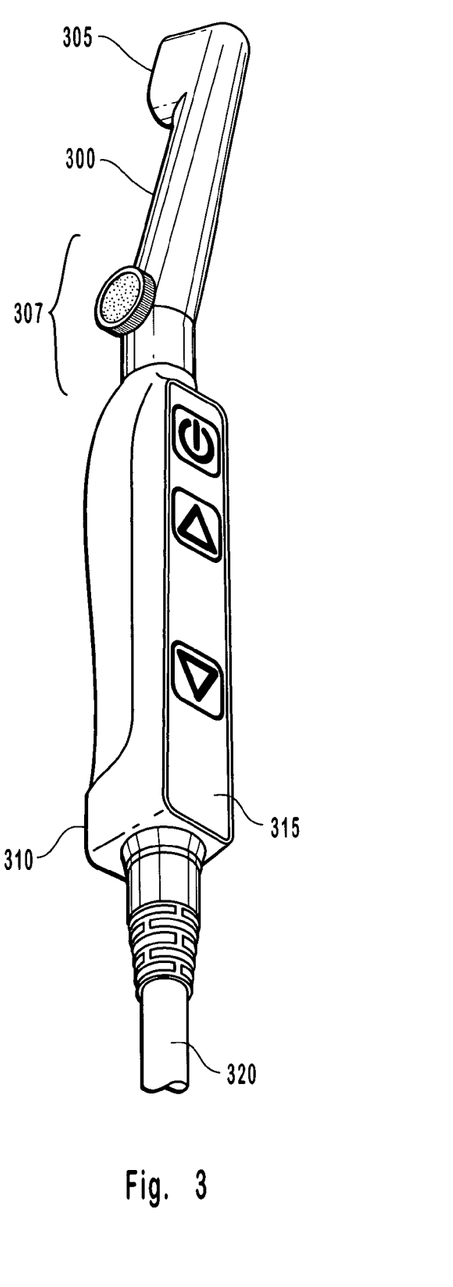
FIG. 3 illustrates an embodiment of the inventive dental device having an adjustment knob.

FIG. 3 shows another embodiment of the present invention with light source 305 disposed on extension portion 300, which connects to handle portion 310 at joint portion 307. FIG. 3 also shows the device with light source controls 315 disposed thereon. The overall device may also have an electricity source, such as cord 320, although any of the preceding and following embodiments may be performed using a battery pack. FIG. 3 shows just one embodiment of how the device may be rotated or may be angled. A manufacturer may wish to supply the device with a turning knob 307 that may increase the angle formed between extension portion 300 and handle portion 310, or a similar adjuster may serve to swivel extension portion 300 compared to handle portion 310 in steady increments. In short, there are several ways well known in the art by which a manufacturer may offer angle or rotation adjustments.

Figure 4:
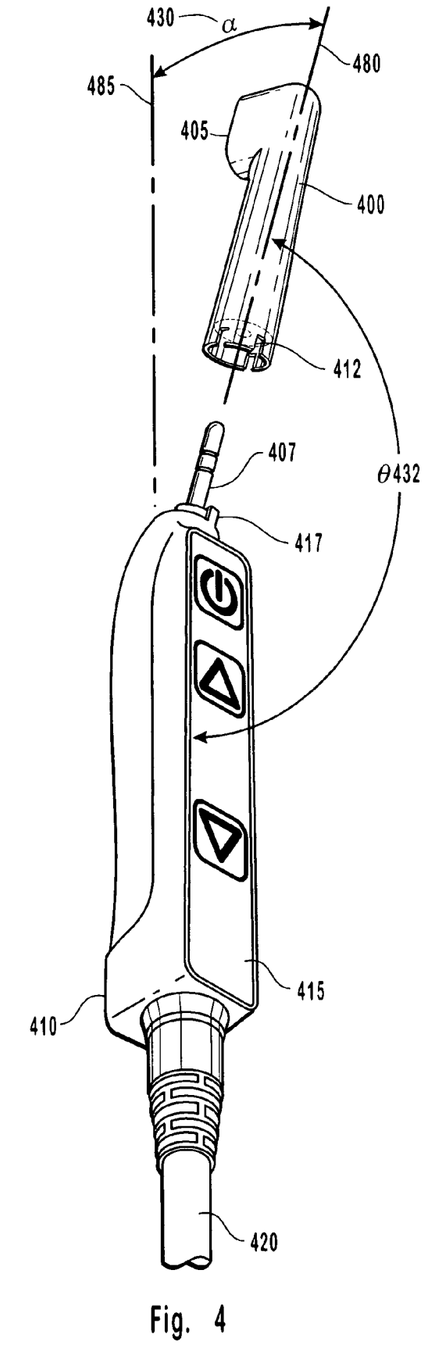
FIG. 4 illustrates one embodiment of the inventive dental device for electrically connecting and/or rotating separable portions along a single conductive pin.

FIG. 4 shows another embodiment of the present invention regarding how extension portion 400 may be electrically connected with handle portion 410. The device may further comprise light controls 415, shown optionally disposed on handle portion 410, and may also comprise a power source, such as cord 420. FIG. 4 shows extension portion 400 conforming substantially along a first longitudinal axis 480 and handle portion 410 conforming substantially along a second longitudinal axis 485. The intersection of these longitudinal axes forms an acute angle α 430, and a corresponding obtuse angle 432. FIG. 4 shows extension portion 400 bending away from handle axis 485, with light source 405 directing light toward handle axis 485, or in a plane formed by the acute angle α 430, and hence in a contra angle position. The joint between extension portion 400 and gripping portion 410, shows an electrical connector 407, which may be a standard electronic mating.

FIG. 4 also shows that the extension portion 400 may be rotatable from handle portion 410 by a series of discrete, separate fittings such as female fit 412 and male fit 417. One will appreciate that male and female rotation fittings provide steady (or locking) rotation increments, and prevent rotation slippage. As well, these fittings may be configured to rotate the extension portion at any variety of rotation degrees. FIG. 4, however, shows two male positions such that a user may rotate extension portion 400 only by 180 degrees. Of course, a manufacturer may configure this to allow rotation by 45 or 90 degree increments, or other more continuous variants.

Figure 5:
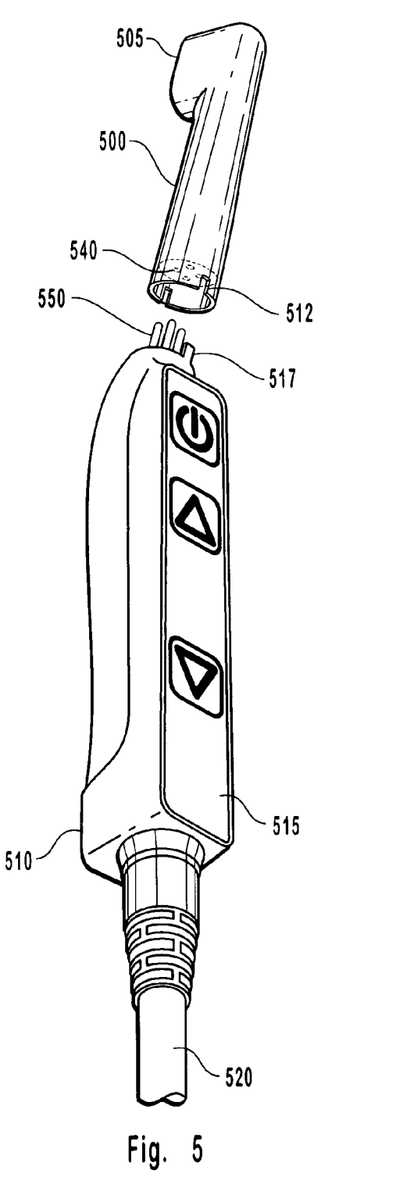
FIG. 5 illustrates another embodiment of the inventive dental device for rotating separable portions and electrically connecting the portions using a plurality of conductive pins.

FIG. 5 shows another embodiment of how the extension portion of the inventive dental device may be connected with the gripping portion, and also be both angled, and rotatable. FIG. 5 shows light source 505 disposed on an extension portion 500, which is connected with gripping portion 510. On gripping portion 510 are light source controls 515 and exemplary power source 520. The extension portion 500 and gripping portion 510 may connect electrically through a plurality of male 550 and female 540 electrical elements. A user may also rotate the extension portion 500 independently with gripping portion 510 via fittings 512 and 517. Again, as in the previous Figures, this may be configured to rotate at 45, 90, and 180 degrees, or more continuous variants in between, etc. Male 550 and female 540 electrical connectors may comprise alternating positive and negative connectors, or uniformly charged male 550 and uniformly charged female 540 electrical connectors, etc.

Figure 6:
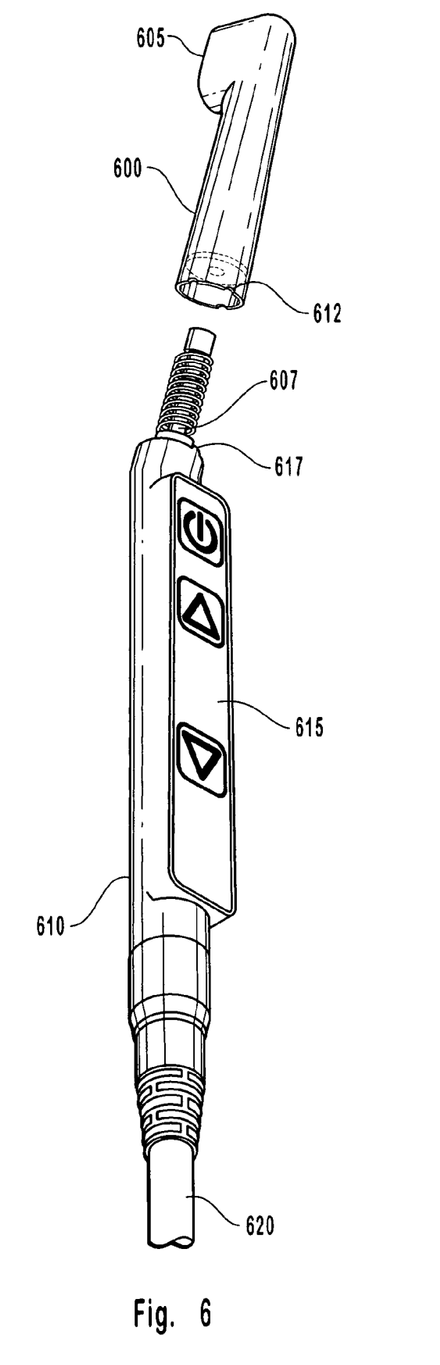
FIG. 6 illustrates one embodiment of the inventive dental device where the portions are not separable, but the portions are rotatable through a spring and fitting means.

FIG. 6 shows one embodiment of the invention where the device is rotatable but not actually separable, though it is shown separated for purposes of convenience. FIG. 6 illustrates a light source 605 disposed on an extension portion 600, which is communicably connected with gripping portion 610. FIG. 6 also shows light source controls 615 disposed on the device, and the device connected electrically with power source 620. At the connection point between extension portion 600 and handle portion 610, shown is an electrical connection 607 surrounded by a spring. In this embodiment, the electrical connection preferably locks the extension portion 600 and handle portion 610 from full lateral separation. Nevertheless, the spring may allow the extension portion 600 to rise away from the gripping portion 610 sufficient that a user may rotate the extension and handle portions with respect to each other.

The degree a user may rotate the respective portions may be governed by mating points between extension portion 600 and gripping portion 610, such as mating portions 612 and 617. As in the previous embodiments, one will appreciate that such mating portions provide a steady, non-slipping rotation capability. Accordingly, a manufacturer may configure the device to allow extension portion 600 rotation from the gripping portion 610 by 45 degrees, 90 degrees, 100 degrees, 180 degrees, etc. The ability to rotate the portions, of course, allows the user of the device to conform the device to a variety of different positions. This, in conjunction with the ability to form a contra angle, also allows the operator a greater ease of use in reaching, for example, light curable dental compounds in certain curved portions of a patient's mouth. Rotation capability allows greater flexibility for use by left and right handed operators to access the same angles alike.

Figure 7:
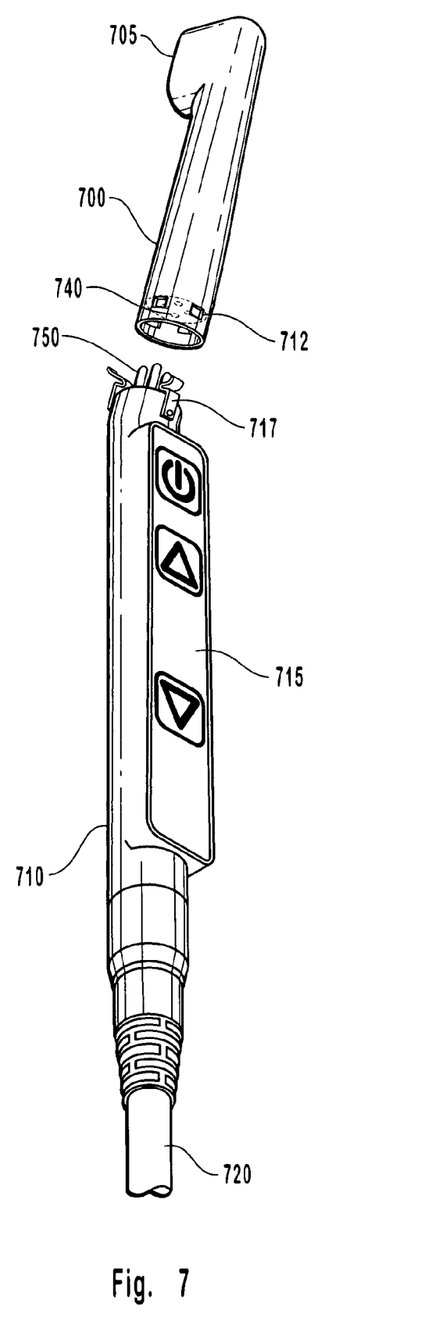
FIG. 7 illustrates another embodiment for rotating and separating the inventive dental device portions with different attachment means.

FIG. 7 shows another embodiment of how this angled device may be configured to both rotate and/or separate the respective device portions. The inventive device as shown in FIG. 7 has light source 705 disposed on an extension portion 700, the extension portion connected to a gripping or handle portion 710. The device also has an electrical connection 720 exposed on gripping portion 710, and a light source control 715 disposed thereon. Electrical female fittings 740 and male fittings 750 comprise a plurality of mated electrical connections, such as shown also in FIG. 5. These electrical fittings may comprise alternating positive and negative connectors, depending on a manufacturer's preference or may be uniformly charged. These provide the electrical connection between handle portion 710 and extension portion 700 so that light source 705 may receive necessary power.

FIG. 7 shows a rotation capability between extension portion 700 and gripping portion 710, along mating portions 712 and 717. This is yet another way of how the extension may be rotated. Here gaps 712 may be configured for 45, 90 degree and 180 rotations, etc., and flexible component 717 is designed to snap into each gap 712. In short, there are many different ways in which to rotate or separate the inventive dental device where at least one of the rotated positions should provide a contra angle for the light source.

Figures 8A, 8B:
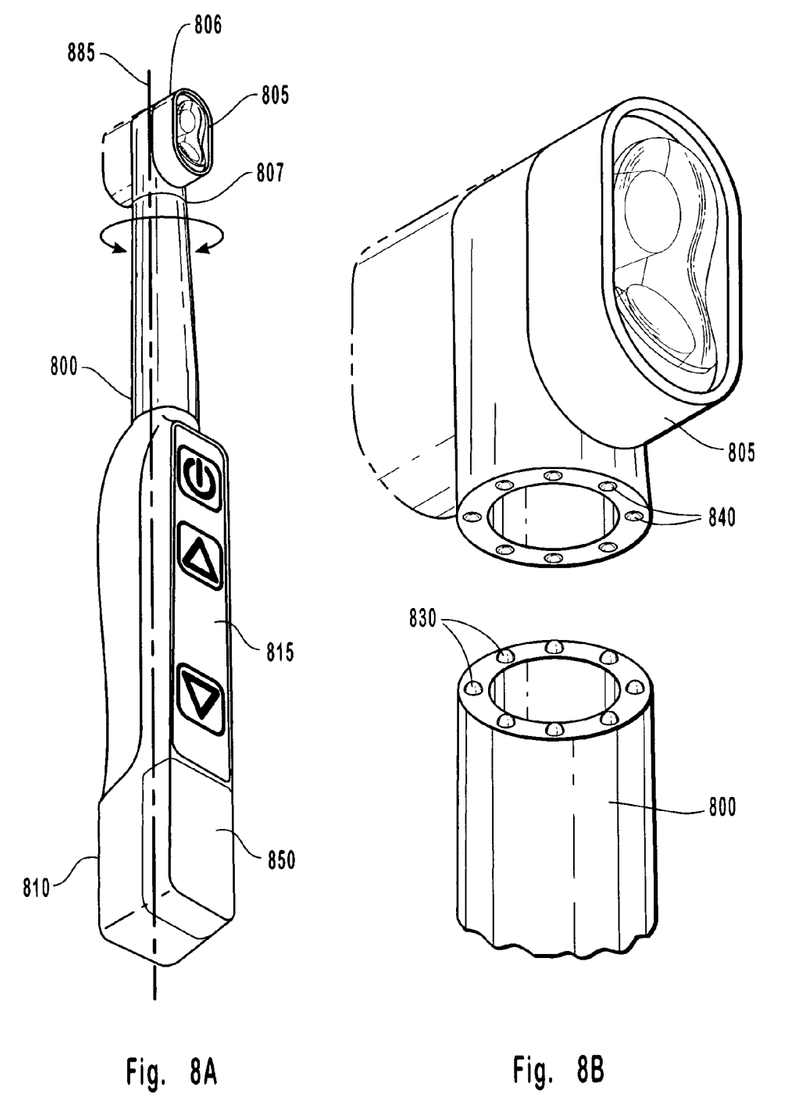
FIGS. 8A–8B illustrate a more linear embodiment of the present invention and a mechanism for twisting the light source without separating the light source from the device.

FIGS. 8A–8B, illustrate yet additional variations on the dental device that may be easily applied to other embodiments described herein, or to other embodiments within the spirit of this disclosure. For example, the dental curing device may be substantially linear, wherein extension portion 800 and handle portion 810 both conform substantially along axis 885. The device may further comprise light controls 815, shown optionally disposed on handle portion 810. Alternatively, it could be said that extension portion 800 and handle portion 810 both conform along substantially parallel axes. In addition, the inventive dental curing device may have a standard battery compartment 850 so that the dental curing device is not limited in motion by an attached power source, e.g., 120 (as shown in FIG. 1A). Of course, the dental curing device may also have both a battery source 850 and a power source 120 such that the dental curing device uses rechargeable batteries that recharge when attached to the power source 120.

FIGS. 8A–8B also illustrate some of the ways the device may be configured to rotate the light source about the longitudinal axis 885 using an additional type of restraint means. In particular, FIG. 8B is an exploded view of one possible restraint/rotation means for rotating light source 805 about the extension portion 800. In FIG. 8A, light source 805 is shown to have an attachment or swivel point 807 that is much higher up along the dental curing device than the swivel point, e.g., 207, shown in other embodiments. In some such embodiments, the extension portion 800 and handle portion 810 may not swivel or detach, though the light source 805 may. Furthermore, light source 805 may itself swivel at a longitudinal swivel point 806 within the light source 805 so that the light source may fan up or down (shown in FIG. 9B), to increase the variety of accessed angles. The ability to swivel the light source about the extension portion 800 may be accomplished by a variety of mechanical methods, though one is shown in FIG. 8B for purposes of convenience, and a second is shown in FIG. 9B.

With respect to the swivel mechanism of FIG. 8B, the swivel point 807 may comprise an upper and lower plate with a plurality of detents 830 that fit conformably into a plurality of corresponding recesses 840, and hence provide restraint means when in position. Thus, the user would simply rotate the light source 805 out of the restraint means by applying transverse pressure, which in turn causes the detents 830 to move out of the original recess 840. Then detents 830 would then fall into the next recess 840, creating a new restraint, when the respective detent 830 and next recess 840 are aligned. Such a motion may create a "click" sound when a user rotates the light source 805. In short, there are a variety of methods for accomplishing restraint/rotation means with a click adjustment.

Figure 9A:
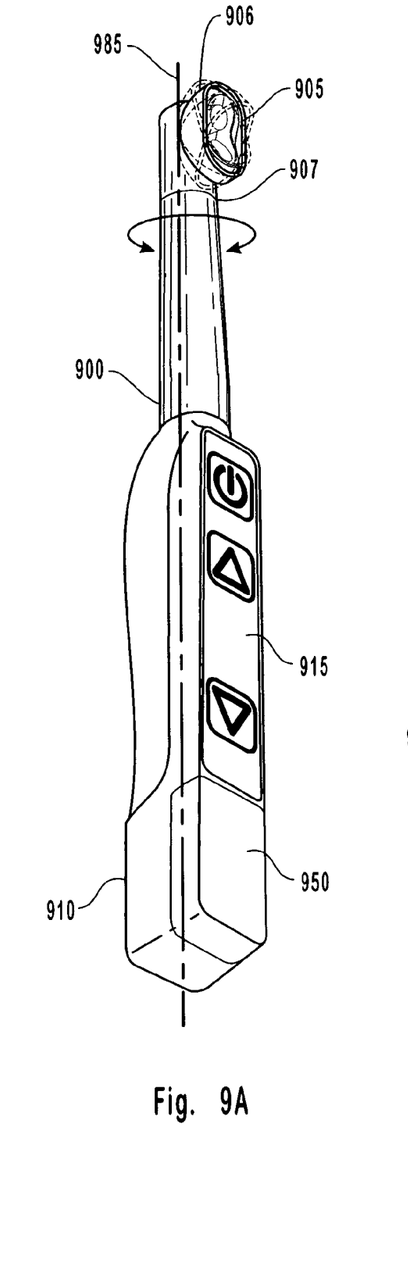
FIGS. 9A–9B illustrate an embodiment of the present invention for adjusting the light source laterally and longitudinally.
Figure 9B:
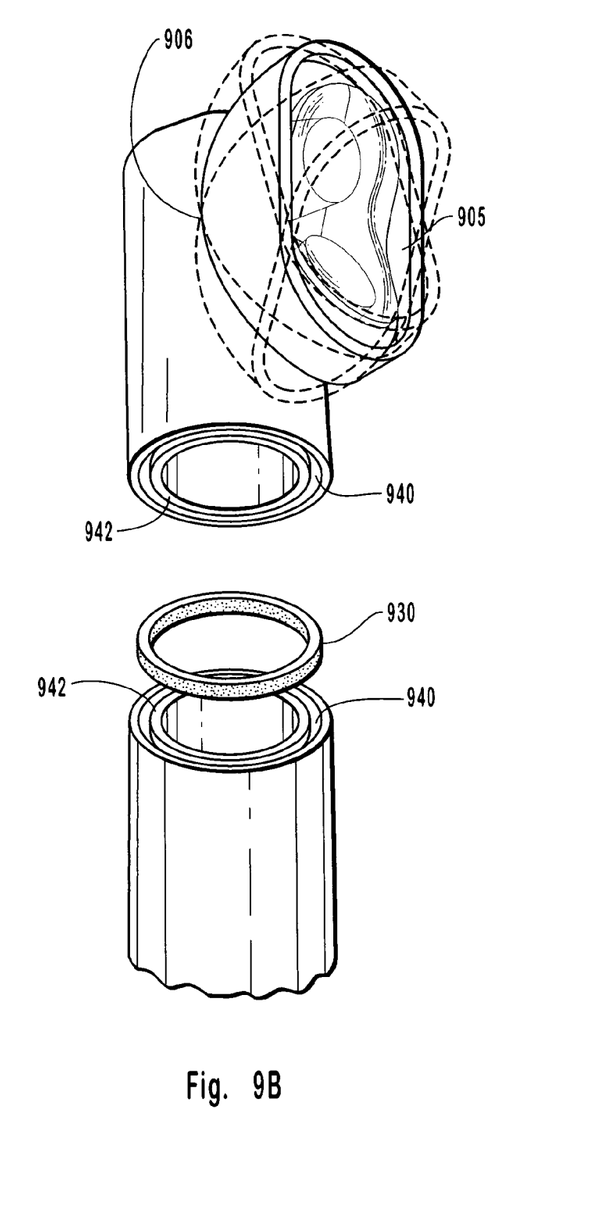

FIGS. 9A–9B illustrate additional embodiments of the present invention for adjusting the light source laterally and longitudinally, and for rotating the light source with respect to the device. FIG. 9A shows a substantially linear light-curing device having a handle 910, a battery compartment 950, and light controls 915. An extension portion 900 is also shown disposed along a handle axis 985, such that the handle 910 and extension 900 portions comprise a substantially linear light curing device. As in FIGS. 8A–8B, light source 905 is shown having a swivel point 907 much higher up along the extension portion 900. FIG. 9A shows an additional swivel point 906 whereby the light source 905 may swivel longitudinally up and down, and hence deliver light through a greater variety of angles.

FIG. 9B illustrates an additional method of rotating the light source transversely with respect to the extension portion 900. This can be accomplished using alternative restraint means, for example, through use of one or more elastomeric rings 930 interfacing between the light source 905 head, and the extension portion 900. A ring 930 may be of sufficient height to extend longitudinally into a ring recess 940, to create a circular friction fit. The recess 930 itself may be created having elastomeric inner rings 942 that rub against ring 930. The light source 905 would then rotate when a user applies sufficient transverse pressure to overcome the friction forces inherent in the elastomeric ring 930 and recess 940. These friction forces should provide sufficient restraint means such that the elastomeric ring 930 would stabilize the light source 905 from rotating against recess 940 while a user applies the curing device within a patient's mouth. This friction based rotation mechanism could provide a more granular rotation mechanism than might be possible with other rotation mechanisms illustrated in the prior figures. In both of the illustrated swivel cases of FIGS. 8A–8B, and 9A–9B, the inventive dental device may be configured to swivel only with no detachment between the light source (805, 905) extension portions (800, 900) and handle portion (810, 910) or to swivel with some moderate detachment, or to detach in accordance with other embodiments described herein.

In summary, the dental devices of the invention are configured to allow at least one contra angle formation for the light source, so that the light source may access the maximum positions within a patient's mouth, while minimizing prior ergonomic disadvantages. The devices are configurable with any number of electrical connections, and, in some cases, any number of rotation mechanisms. Such rotation mechanisms may include the above, and may also include other steady rotation mechanisms known in the art such as those employing friction. In addition, the devices are configured to have the same general shape, size and weight of conventional dental hand pieces, thereby enabling the dental devices to be securely held within the holders or holding slots of conventional dental hand piece holding trays. The dental devices of the invention may also include a remotely located power supply, which generally eliminates the need for such items as battery packs and fiber optic light guides, thereby reducing the overall weight and bulk of the dental devices.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

We claim:

1. A dental curing light for use in photo curing light-curable dental compounds, comprising:
   a handle portion extending at least approximately along a first longitudinal axis;
   an extension portion extending at least approximately along a second longitudinal axis so that the second longitudinal axis is laterally offset by a predetermined angle relative to the first longitudinal axis, and wherein the extension portion is rotatably connected and rotatably adjustable relative to the handle portion in order to selectively alter the predetermined angle; and
   a light source disposed on a side of the extension portion so that light is emitted laterally from the extension portion when the curing light is in use,
   wherein by rotating the extension portion to alter the predetermined angle an angle is selected to facilitate placement of the light source near at least one tooth to be treated.

2. A dental curing light as defined in claim 1, wherein the handle portion and extension portion are configured so as to approximate the size and shape of a standard dental hand piece.

3. A dental curing light as defined in claim 1, wherein the handle portion is substantially linear.

4. A dental curing light as defined in claim 3, the handle portion further comprising one or more controls on a top surface of the handle portion.

5. A dental curing light as defined in claim 4, wherein a portion of a bottom surface of the handle portion is curved so as to provide a comfortable grip.

6. A dental curing light as defined in claim 1, wherein the extension portion is substantially linear.

7. A dental curing light as defined in claim 1, wherein the predetermined angle approximates the contra angle of a standard dental hand piece.

8. A dental curing light as defined in claim 7, wherein the predetermined angle is about 17.5°.

9. A dental curing light as defined in claim 7, wherein the light source is positioned so as to emit light approximately perpendicular to the extension portion.

10. A dental curing light as defined in claim 1, wherein the extension portion is movable relative to the handle portion in order to selectively position the extension portion in one of a plurality of different conformations relative to the handle portion in order to alter the predetermined angle.

11. A dental curing light as defined in claim 1, wherein the extension portion is positionable in at least one conformation relative to the handle portion in order for the light source to emit light at an obtuse angle relative to the first longitudinal axis.

12. A dental curing light as defined in claim 1, wherein the extension portion is positionable in at least one conformation relative to the handle portion in order for the light source to emit light at an acute angle relative to the first longitudinal axis.

13. A dental curing light as defined in claim 1, wherein the extension portion is laterally adjustable relative to the handle portion.

14. A dental curing light as defined in claim 1, the dental curing light further comprising rotation restraint means for maintaining the extension portion at a desired rotational angle relative to the handle portion during use.

15. A dental curing light as defined in claim 14, the rotation restraint means comprising at least one of a mechanical locking device, one or more locking pins that fit into one or more corresponding recesses, or a friction fit.

16. A dental curing light as defined in claim 1, the light source comprising at least one LED or LED array.

17. A dental curing light for use in photo curing light-curable dental compounds, comprising:
   a handle portion extending at least approximately along a first longitudinal axis;
   an extension portion extending at least approximately along a second longitudinal axis so that the second longitudinal axis is laterally offset by a predetermined angle relative to the first longitudinal axis, the predetermined angle comprising an angle at which light may be emitted relative to the handle portion, and the predetermined angle approximating the contra angle of a standard dental hand piece;
   a light source disposed on a side of the extension portion so that light is emitted laterally from the extension portion when the curing light is in use, and
   wherein at least one of the extension portion and light source is rotatably connected and rotatably adjustable relative to the handle portion in order to selectively alter the predetermined angle at which light may be emitted.

18. A dental curing light as defined in claim 17, at least one of the extension portion and light source is positionable in at least one conformation relative to the handle portion in order for the light source to emit light at an acute angle relative to the handle portion.

19. A dental curing light as defined in claim 18, the light source comprising at least one LED or LED array.

20. A dental curing light for use in photo curing light-curable dental compounds, comprising:
   a handle portion extending at least approximately along a first longitudinal axis;
   an extension portion extending at least approximately along a second longitudinal axis that is either co-linear or parallel with the first longitudinal axis so that the extension portion is substantially linear with the handle portion;
   a light source disposed on a side of the extension portion so that light is emitted laterally from the extension portion when the curing light is in use, and
   wherein the light source is connected to the extension portion at a first swivel point that permits the light source to be rotatably adjusted relative to the handle portion.

21. A dental curing light as defined in claim 20, wherein the light source is connected to the extension portion at a second swivel point that permits the light source to swivel longitudinally up and down so as to permit the light source to be adjusted to emit light at any of a plurality of angles, at least one of which comprises an angle that approximates the contra angle of a standard dental hand piece when in use.

22. A dental curing light as defined in claim 20, the light source comprising at least one LED or LED array.

23. A dental curing light for use in photo curing light-curable dental compounds, comprising:
   a handle portion extending at least approximately along a first longitudinal axis;
   an extension portion extending at least approximately along a second longitudinal axis and being rotatably connected to the handle portion in a manner so that the extension portion can be selectively rotated relative to the handle portion without being completely detached from the handle portion;
   a light source disposed at an end of the extension portion distal to the handle portion and positioned so that the light source emits light laterally relative to the extension portion when in use; and
   rotation restraint means for maintaining the extension portion at a desired rotational angle relative to the handle portion during use.

24. A dental curing light as defined in claim 23, wherein the second longitudinal axis is laterally offset by a predetermined angle relative to the first longitudinal axis.

25. A dental curing light as defined in claim 24, wherein the predetermined angle approximates the contra angle of a standard dental hand piece when the extension portion is selectively rotated into at least one angle of rotation relative to the handle portion.

26. A dental curing light as defined in claim 23, wherein the second longitudinal axis is substantially parallel to the first longitudinal axis.

\* \* \* \* \*

UNITED STATES PATENT AND TRADEMARK OFFICE
CERTIFICATE OF CORRECTION

PATENT NO. : 7,192,276 B2
APPLICATION NO. : 10/644707
DATED : March 20, 2007
INVENTOR(S) : Fischer et al.

It is certified that error appears in the above-identified patent and that said Letters Patent is hereby corrected as shown below:

Title Page
Page 2, Reference 2001/0055451, change "Kubara" to --Kuhara--

Column 5
Line 9, change "angle 432" to --angle θ 432--

Column 6
Line 36, after "FIGS. 8A-8B", remove [,]

Signed and Sealed this

Twenty-second Day of July, 2008

JON W. DUDAS
*Director of the United States Patent and Trademark Office*